United States Patent
Chatellier et al.

(10) Patent No.: US 6,681,632 B2
(45) Date of Patent: Jan. 27, 2004

(54) METHOD FOR EVALUATING THE RESILIENCE OF A WELDED ASSEMBLY AND CORRESPONDING ANALYSIS APPARATUS MEASURING THE SPEEDS OF ULTRASONIC SURFACE WAVES

(75) Inventors: Jean-Yves François Roger Chatellier, Arcueil (FR); Daniel Sébastien Ramahefasolo, Echarcon (FR)

(73) Assignee: SNECMA Moteurs, Tokyo (JP)

(*) Notice: Subject to any disclaimer, the term of this patent is extended or adjusted under 35 U.S.C. 154(b) by 0 days.

(21) Appl. No.: 09/926,593

(22) PCT Filed: Mar. 22, 2001

(86) PCT No.: PCT/FR01/00874

§ 371 (c)(1),
(2), (4) Date: Nov. 23, 2001

(87) PCT Pub. No.: WO01/71339

PCT Pub. Date: Sep. 27, 2001

(65) Prior Publication Data

US 2002/0134157 A1 Sep. 26, 2002

(30) Foreign Application Priority Data

Mar. 23, 2000 (FR) .............................................. 00 03696

(51) Int. Cl.[7] .............................................. G01H 1/00
(52) U.S. Cl. .............................. 73/579; 73/597; 73/598; 73/602
(58) Field of Search ........................ 73/579, 597, 598, 73/600, 602, 643, 628, 644, 645

(56) References Cited

U.S. PATENT DOCUMENTS

| | | | | |
|---|---|---|---|---|
| 3,850,028 A | * | 11/1974 | Thompson et al. | 73/643 |
| 3,868,847 A | * | 3/1975 | Gunkel | 73/622 |
| 4,144,766 A | * | 3/1979 | Wehrmeister | 73/587 |
| 4,372,163 A | * | 2/1983 | Tittmann et al. | 73/602 |
| 5,085,082 A | * | 2/1992 | Cantor et al. | 73/622 |
| 5,408,882 A | | 4/1995 | McKinley et al. | 73/597 |
| 5,439,157 A | * | 8/1995 | Geier et al. | 228/9 |
| 5,474,225 A | * | 12/1995 | Geier et al. | 228/104 |
| 5,537,876 A | * | 7/1996 | Davidson et al. | 73/624 |
| 5,760,307 A | * | 6/1998 | Latimer et al. | 73/643 |
| 5,866,820 A | * | 2/1999 | Camplin et al. | 73/643 |
| 5,920,014 A | | 7/1999 | Waschkies | 73/597 |
| 6,105,341 A | * | 8/2000 | Campbell | 53/432 |

FOREIGN PATENT DOCUMENTS

DE 196 12 925 5/1997

* cited by examiner

Primary Examiner—Hezron Williams
Assistant Examiner—Jacques Saint-Surin
(74) Attorney, Agent, or Firm—Oblon, Spivak, McClelland, Maier & Neustadt, P.C.

(57) ABSTRACT

Ultrasonic waves are produced at the surface of a thin metal sheet (27) welded to a substrate (28): it was noted that the speed of propagation of the surface waves could then be correlated to the resilience of the welded assembly to enable non-destructive monitoring.

9 Claims, 3 Drawing Sheets

METHOD FOR EVALUATING THE RESILIENCE OF A WELDED ASSEMBLY AND CORRESPONDING ANALYSIS APPARATUS MEASURING THE SPEEDS OF ULTRASONIC SURFACE WAVES

The invention relates to a method for evaluating the resilience of a welded assembly, together with a measuring device applicable to this method and applied to the measurement of speeds of ultrasonic surface waves.

The resilience of a mechanical part is the energy required to rupture it. It can be evaluated by tests carried out on test pieces representative of the assembly and respecting certain standards in specialised instruments like the Charpy machine. It is evident that the manufacture of test pieces and the utilisation of a machine are restricting and that methods more easy to apply, in particular non-destructive monitoring through which the resilience could be evaluated indirectly, would be advantageous.

Such an indirect method for evaluating resilience has been designed and is the aim of this invention. It rests on using ultrasonic surface waves and is applied to a special family of parts: welded assemblies, in particular without addition of material, by diffusion or by analogous methods, of a somewhat thin sheet on a substrate which can be another sheet or a thicker part.

Ultrasonic tests are normally carried out after plunging the part to be analysed into a liquid. Ultrasounds are emitted in the liquid towards the part, and they can be reflected or absorbed by the latter when they reach it. For certain favourable angles of incidence, they can also undergo a conversion of the propagation mode and propagate to the surface of the part, without penetrating further than a shallow depth, providing surface waves called Rayleigh waves. Inventors' research has demonstrated that these surface waves could be correlated to the quality of welding of the assemblies mentioned above, and more precisely that a parameter linked to the speed of propagation of these waves in these assemblies could have a correlation with their resilience, the welding affecting the wave propagation and this parameter in function of its quality.

In its most general form, the invention is a method for evaluating the resilience of a welded assembly of a metal sheet on a substrate, characterised in that it consists of producing ultrasonic surface waves on the sheet, to measure a speed of said waves then to deduce a speed parameter, and to deduce the resilience of the assembly according to a correlation function, obtained beforehand on calibration test pieces comprising a similar welded assembly, which links resilience of calibration test pieces to the speed parameter of calibration test pieces.

Preferably, two speeds of these waves are measured on the welded assembly, along the two principal directions of the sheet, because of its anisotropy. The inventors consider that the speed parameter should be deduced from the slower of the two speeds. This parameter can be a difference in the speed of ultrasonic waves measured on the metal sheet of the welded assembly and on a reference piece made out of the basic material of the sheet metal but without the welded assembly. Then it is suitable that the speeds for which the calculation is made are measured under the same conditions, that is to say that they involve the same measurement direction on the sheet metal of the welded assembly and the metal sheet of the reference piece.

Another aspect of the invention is a measuring instrument applicable to this method; it consists of an instrument for measuring the speed of ultrasonic surface waves on a part, comprising an emission head for waves directed towards the part but at an inclination, characterised in that it comprises a second head, destined either to collect a portion of the waves diffused from the part, or to return said portion towards the emission head as an echo, the second head being directed towards the part but with an inclination opposite to that of the inclination of the emission head, and comprising two active faces, in order to collect or to return said portion of waves, arranged in steps and at an identical distance from the part.

Advantageously, it comprises a frame and head support mechanisms on the frame, designed in such a way as to enable adjustment of the inclination of the heads; and it is recommended that the active surfaces are cylindrical with parallel axes and of the same radius.

The invention will now be described referring to the figures, in which.

Figure 1:
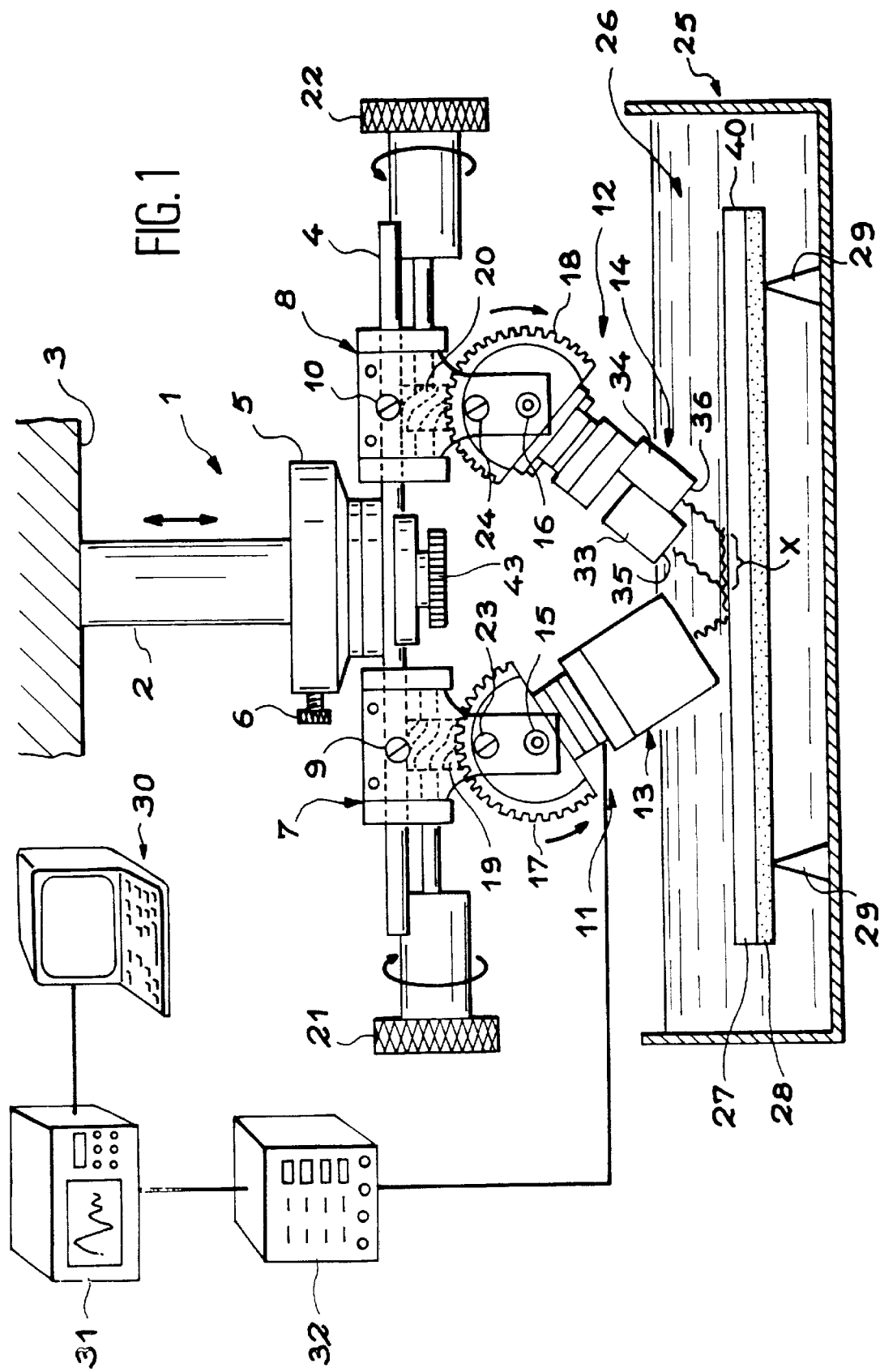
FIG. 1 is a general view of the machine used.

The machine used comprises a frame 1 able to be composed of a vertical suspension column 2 at a fixed point 3 and a guideway 4 linked to the column 2 through the intermediary of a slide 5 able to be fixed at a determined place on the column 2 by a pressure screw 6. Two pointers 7 and 8 are placed on opposite sides of the guideway 4 and can be kept in place by pressure screws 9 and 10. Each of them has a measuring head, referenced respectively 11 and 12, and whose essential element is an ultrasonic sensor 13 for the first and a reflector 14 for the second. The heads 11 and 12 are mounted on the pointers 7 and 8 by horizontal pivots 15 and 16, parallel to each other and perpendicular to the direction of the guideway 4, and they are provided with toothed sectors 17 and 18 forming racks engaging with worm screws 19 and 20 operated by adjusting handles 21 and 22 attached to the pointers 7 and 8 so that the heads 11 and 12 can be set at the chosen inclinations, but opposite to each other so that the sensor 13 and the reflector 14 are pointed in descending and converging directions. Other fixation screws 23 and 24 for blocking the heads 11 and 12 on the pointers 7 and 8 make it possible to stop unwanted rotations of the toothed sectors 17 and 18 relative to the pointers 7 and 8 when the desired inclination has been reached. Finally, a flywheel 43 placed under the slide 5 makes it possible to turn the guideway 4 in a horizontal plane.

In the embodiment illustrated here, the sensor 13 is assigned both to emit ultrasounds and to collect the echoes, as is often the case in this technique, and the reflector 14 is assigned to produce these echoes; meanwhile it is possible to replace the reflector 14 by a pair of sensors in a way described below without the measuring principle being modified.

The machine overhangs a measuring tank 25 partially filled with water, in such a way that the sensor 13 and the reflector 14 are partially immersed and so that the ultrasonic waves used do not exit from the liquid; the part being studied by the machine is a welded assembly 26, composed of a fairly thin metal sheet 27 set on top, facing the sensor 13 and the reflector 14, and of a substrate 28 which can be another metal sheet or a thicker part. The soldered assembly 26 is set on blocks 29 at the bottom of the tank 25.

The sensor 13 is connected to a control console 30 by means of an oscilloscope 31 intended to display the results and by a pulse generator 32. The sensor 13 emits an ultrasonic wave obliquely in the water so that it reaches the metal sheet 27. If the angle of inclination θ of the head 11 and the direction of the waves is well chosen (about 30°), the wave is transmitted to the metal sheet 27 in the form of a Rayleigh surface wave located on the upper face of the metal sheet 27 and at shallow depth, which still reaches the welding since the sheet 27 is fairly thin. The wave is directed towards the edge of the sheet 27, but nonetheless part is diffused upwards, at an angle corresponding to the value θ given above, and symmetrical to the direction of incidence of the waves relative to the vertical.

The reflector 14 is composed of two prisms 33 and 34, whose lower surfaces 35 and 36, turned towards the metal sheet 27, reflect the ultrasounds. If these surfaces are perpendicular to the direction of diffusion of the surface wave upwards, the wave portion thus diffused in sent back as an echo by the prisms 33 and 34 towards the metal sheet 27, before forming a return Rayleigh surface wave, part of which is diffused according to the same principle towards the sensor 13. The outgoing and incoming wave paths are absolutely identical. Thus the sensor 13 registers two echoes corresponding to wave reflections on the reflecting surfaces 35 and 36, and these echoes are distant by the time t needed for the wave to travel twice the distance X (outgoing plus incoming) separating the parts of the metal sheet 27 from where the wave portions are diffused towards these surfaces 35 and 36.

Figure 2:
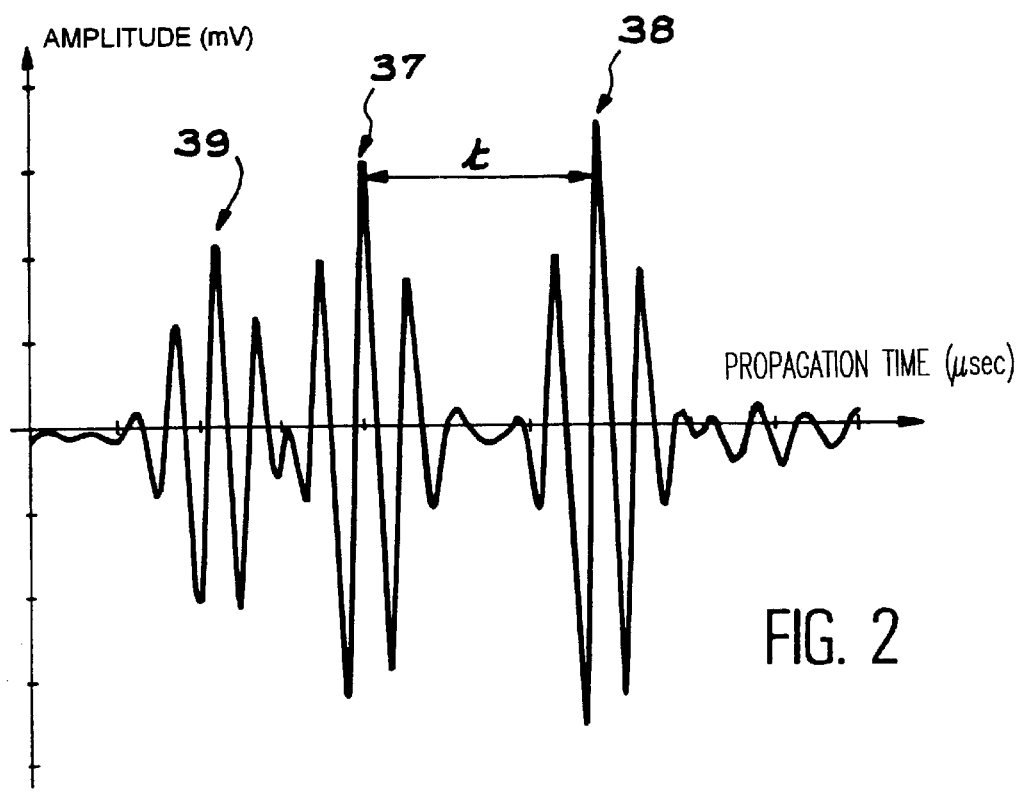
FIG. 2 is a record of measurements.

The two echoes are referenced 37 and 38 on the record provided by the oscilloscope 31 and shown in FIG. 2. They can be identified easily because they are similar: other echoes such as 39, produced by a reflection of the wave on the edge 40 of the metal sheet 27, and which can return to the sensor 13 before the above echoes because of the greater speed of the wave through solids, can also be seen but are not relevant to the method.

Preliminary regulating tests are carried out by adjusting the inclinations of the heads 11 and 12 to increase the echoes 37 and 38 by provoking the most complete mode conversions before proceeding to tests in the way indicated above in order to calculate the speed of propagation of the surface waves in the metal sheet 27 according to the formula $V=2X/t$: the travel time of the waves in the liquid is not taken into consideration since the reflecting surfaces 35 and 36 are stepped so that they are placed substantially at the same distance from the metal sheet 27 at inclination θ.

Figure 3:
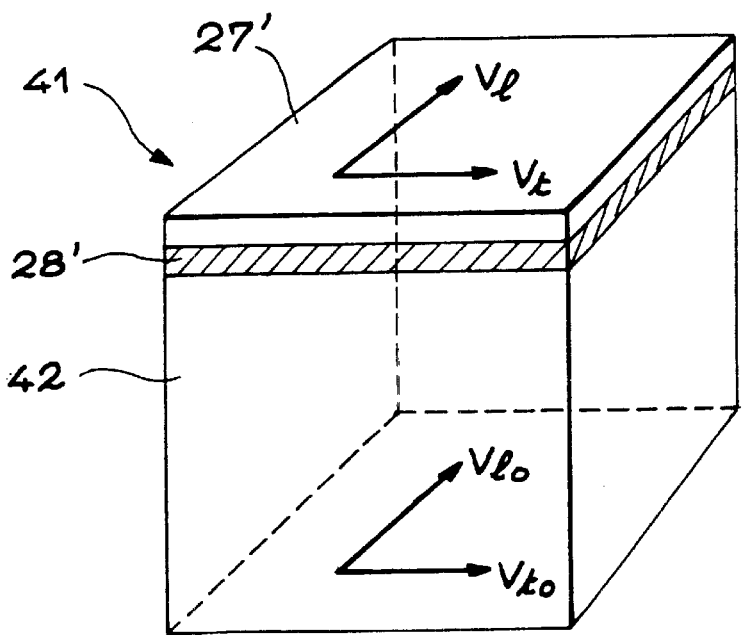
FIG. 3 shows a reference piece or a test piece.

In practice, one can proceed to trials with more complex test pieces such as that 41 shown in FIG. 3. It is composed of a metal sheet 27' similar to the metal sheet 27 (that is of the same thickness, the same composition, and manufactured in the same way), with a substrate 28' similar to substrate 28 in composition and with a lower layer 42 formed of the base material of the metal sheet 27 (or 27'), thus it has the same composition and has been manufactured in the same way wile being much thicker. It is welded to the face of the substrate 28' opposite to that of the metal sheet 27'.

The test pieces 41 put under the machine in place of the welded assembly 26 make it possible to measure successively the speeds Vl and Vt of the surface ultrasounds in the two principal directions of the metal sheet 27', longitudinal and transversal, and then the corresponding speeds Vl0 and Vt0 of the lower layer 42 after turning over the test piece 41. The principal directions are controlled by the direction of rolling of the metal sheet 27'. In fact, the rolling produces an anisotropy in the metal sheets and thus fairly noticeable differences between Vl and Vt or Vl0 and Vt0. The values Vl and Vt are influenced by the welding used between 27' and 28', while the values Vl0 and Vt0 express the intrinsic properties of the base material of the lower layer 42, whose thickness is too high for the waves to penetrate as far as the welding with the substrate 28'. It should be noted that it is possible to carry out these measurements without welding the substrate 28' to the lower layer 42: then, in addition to the welded assemblies 26, one uses the lower layer 42 separately, to calculate Vl0 and Vt0.

Next one chooses the lowest speed from Vl and Vt, and again the lowest speed from Vl0 and Vt0, for each test piece 41 and one subtracts these lowest values from each other to obtain a parameter ΔV which is very well correlated to the resilience of the assembly welded between the metal sheets 27' and the substrate 28'. This resilience is measured by a mechanical test carried out on the Charpy machine or another suitable machine. These tests are normalised and carried out in the usual way, and thus there is no need to describe them here. The test pieces used for these mechanical measurements must be similar to the welded assemblies 26 for which one has measured Vl and Vt, that is to say the metal sheet, the substrate and their welding conditions must be the same.

Figure 4:
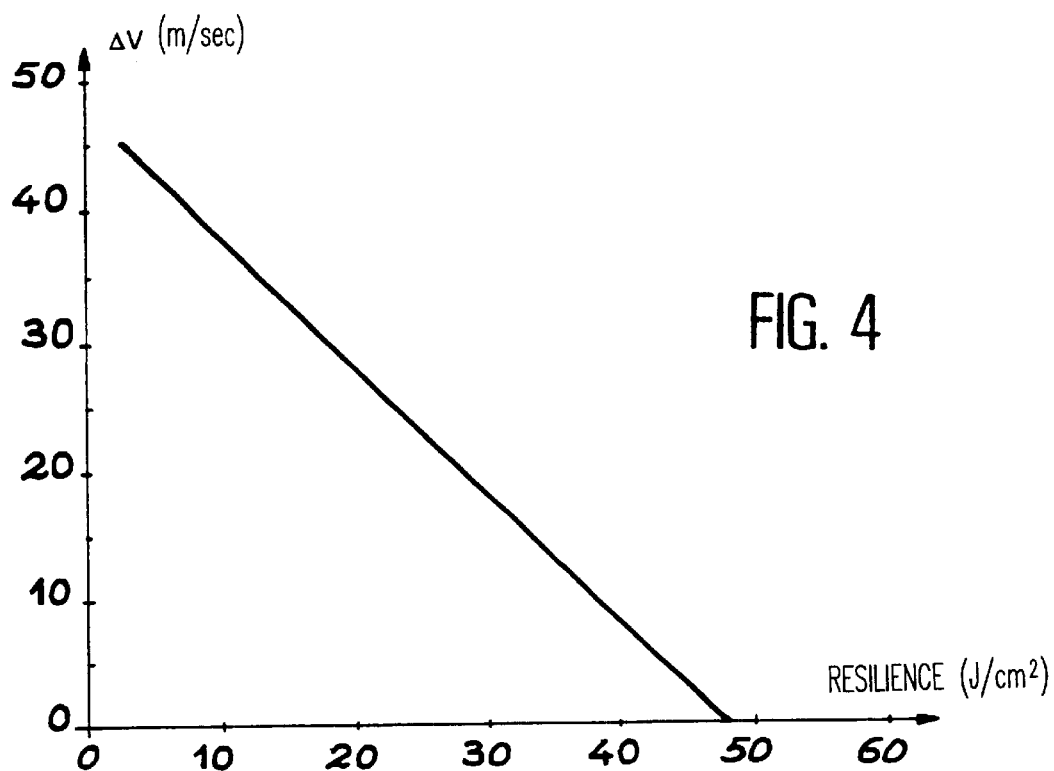
FIG. 4 is a concrete example of a correlation function obtained.

FIG. 4 shows that a linear correlation was found between the difference in slow speeds ΔV (in m/sec) as defined above and the resilience R (in $J/cm^2$) for the welded joints of metal sheets in titanium alloys.

When the correlation function has been obtained by means of calibrations made with test pieces 41 or 26, under different welding conditions to obtain several points for this function, non-destructive monitoring is possible on other test pieces for which ΔV is measured: the resilience R is then read from the correlation graphic.

Figure 5:
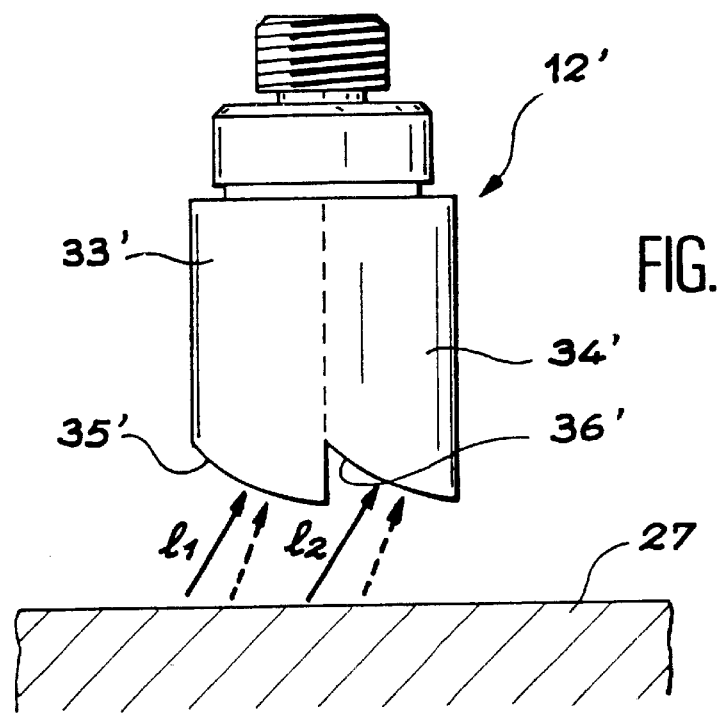
FIG. 5 shows an upgrading of the machine.

A refinement of the machine will finally be described with reference to FIG. 5: it consists of an improved design of the second head 12 dealing with the reflection, in which the prisms 33 and 34 are replaced by prisms 33' and 34' whose reflecting surfaces 35' and 36' are no longer plane but cylindrical, with axes parallel to the pivot 16 and equal radii: the waves diffused between the metal sheet 27 and these reflecting surfaces 35' and 36' are always returned in the same direction at inclination θ, which avoids adjusting the inclination of this modified reflector.

The method makes it possible to carry out measurements in several places of the welded assembly, and thus to assess its uniformity.

What is claimed is:

1. Method for evaluating the resilience of a welded assembly of a metal sheet on a substrate, a welding of the assembly having been created by diffusion or another process without addition of material, comprising the steps of:
    producing ultrasonic waves on the metal sheet said waves being surface waves located near an upper surface of the metal sheet but reaching the welding,
    measuring a speed of said waves,
    selecting at least one portion of a received signal which comprises a part of said waves, and
    deducing a speed parameter (ΔV) from a receiving time of said at least one portion to deduce the resilience of the assembly according to a correlation function already obtained on test pieces comprising a similar welded assembly, which links the resilience of the test pieces to the speed parameter of the test pieces.

2. Method for evaluating resilience of a welded assembly according to claim 1, further comprising measuring two speeds of said waves on the welded assembly, one speed in each of two principal directions of the metal sheet.

3. Method for evaluating the resilience of a welded assembly according to claim 2, wherein the speed parameter is deduced from that of the lower of the two speeds.

4. Method for evaluating the resilience of a welded assembly according to claim 3, wherein the speed parameter is a speed difference between surface ultrasonic waves on the metal sheet of the welded assembly and on a part made in the base material of the metal sheet.

5. Method for evaluating the resilience of a welded assembly according to claim 4, wherein the difference in speeds is calculated for that of the slower of the two speeds on the welded assembly, and that of the slower of the two speeds measured in the two principal directions of the part made in the base material of the metal sheet.

6. Apparatus for measuring the speed of surface ultrasonic waves on a part, comprising an emission head of waves directed towards the part but with an inclination, a second head, assigned either to collect a portion of the waves diffused from the part, or to return said portion to the emission head as an echo, the second head being directed towards the part but with an inclination opposite to the inclination of the emission head, and two active faces configured to collect or to return said wave portion, in a stepped arrangement and at an identical distance from the part.

7. Apparatus for measuring the speed of surface ultrasonic waves according to claim 6 further comprising a frame and support mechanisms for the heads on the frame, configured to adjust the inclination of the heads.

8. Apparatus for measuring the speed of surface ultrasound waves according to claim 6, wherein the active surfaces are cylindrical with parallel axes and have a same radius.

9. Apparatus for measuring the speed of surface ultrasonic waves according to claim 6, wherein the heads are mounted on a support pivoting in a horizontal plane.

\* \* \* \* \*